US00PP26625P3

(12) United States Plant Patent
Klemm et al.

(10) Patent No.: US PP26,625 P3
(45) Date of Patent: Apr. 19, 2016

(54) POINSETTIA PLANT NAMED 'NPCW13218'

(50) Latin Name: *Euphorbia pulcherrima*
Varietal Denomination: NPCW13218

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 154 days.

(21) Appl. No.: 13/998,917

(22) Filed: Dec. 18, 2013

(65) Prior Publication Data
US 2015/0173285 P1 Jun. 18, 2015

(51) Int. Cl.
*A01H 5/02* (2006.01)

(52) U.S. Cl.
USPC ..... Plt./307

(58) Field of Classification Search
USPC ..... Plt./307
See application file for complete search history.

*Primary Examiner* — Keith Robinson
(74) *Attorney, Agent, or Firm* — Barbara Campbell; Bethany R. Roahrig; Cochran Freund & Young, LLC

(57) ABSTRACT

A new poinsettia plant particularly distinguished by having bright red bracts, a triangular plant form, and an upright growth habit, is disclosed.

1 Drawing Sheet

Genus and species: *Euphorbia pulcherrima.*
Variety denomination: 'NPCW13218'.

BACKGROUND OF THE NEW PLANT

The present invention comprises a new and distinct variety of poinsettia, botanically known as *Euphorbia pulcherrima* and hereinafter referred to by the variety name 'NPCW13218'. 'NPCW13218' was derived as a selection of a single, bright red plant among a population derived from irradiated cuttings of the poinsettia 'NPCW10164' (U.S. Plant Pat. No. 22,597) and commercially known as 'Christmas Day', having red bracts.

In November 2010, a single bright red plant was selected in Stuttgart, Germany from irradiated lines of poinsettia 'NPCW10164'. In February 2011, 'NPCW13218' was first asexually propagated by vegetative cuttings. 'NPCW13218' was found to reproduce true to type in successive generations of asexual propagation via vegetative cuttings in Stuttgart, Germany.

CROSS REFERENCE TO RELATED APPLICATIONS

Plant Breeder's Rights for 'NPCW13218' were applied for in Europe on Dec. 9, 2013, File No. 2013/3123, and Grant No. 41415. 'NPCW13218' has not been made publicly available or sold more than one year prior to the filing date of this application.

SUMMARY

The following are the most outstanding and distinguishing characteristics of this new variety when grown under normal horticultural practices in Stuttgart, Germany.

1. Bright red bracts;
2. A triangular plant form; and
3. An upright growth habit.

DESCRIPTION OF THE PHOTOGRAPH

This new poinsettia plant is illustrated by the accompanying photograph which shows an overall view of the plant. The photograph is of a plant approximately four-months-old grown indoors in Stuttgart, Germany in November 2013.

The colors shown are as true as can be reasonably obtained by conventional photographic procedures.

DESCRIPTION OF THE NEW VARIETY

The following detailed descriptions set forth the distinctive characteristics of 'NPCW13218'. The data which define these characteristics were collected from asexual reproductions carried out in Stuttgart, Germany. Data was collected on four-month-old plants grown indoors in Stuttgart, Germany under greenhouse conditions in the fall of 2013. Color references are to The R.H.S. Colour Chart of The Royal Horticultural Society of London (R.H.S.), $5^{th}$ edition (2007).

Classification:
- *Family.*—Euphorbiaceae.
- *Species.*—*Euphorbia pulcherrima.*
- *Common name.*—Poinsettia.
- *Variety.*—'NPCW13218'.

Parentage: Selection from the irradiated Poinsettia 'NPCW10164'.

Growth:
- *Time to produce a rooted cutting.*—4 weeks.
- *Blooming habit.*—Intermittent.
- *Flowering response time.*—Approximately 53 days.
- *Keeping quality.*—Very good.

Plant description:
- *Form.*—Triangular.
- *Growth habit.*—Upright.
- *Height.*—28.0 cm to 30.0 cm.
- *Width.*—25.0 cm to 30.0 cm.

*Number of branches.*—5 to 6.
*Average number of inflorescences per plant.*—5.5.
*Disease and pest resistance.*—None observed.

Propagation:
*Type cuttings.*—Apical cuttings.
*Time to produce a rooted cutting.*—4 weeks.
*Rooting habit and root color.*—Freely branching and white.

Lateral branches:
*Color.*—RHS 143A.
*Length.*—25.0 cm.
*Internode length.*—1.2 cm to 3.5 cm.
*Diameter.*—0.5 cm to 0.8 cm.
*Branching habit.*—Freely branching.
*Number of lateral branches per plant.*—5 to 6.
*Texture.*—Smooth.

Leaves:
*Quantity.*—6 to 7 per lateral branch.
*Arrangement.*—Alternate.
*Number of lobes on the leaf blade.*—1 to 3.
*Depth of the deepest sinus of the leaf blade.*—0.5 cm.
*Shape.*—Ovate.
*Apex.*—Acute.
*Base.*—Obtuse.
*Margin.*—Serrate.
*Length.*—8.0 cm to 14.0 cm.
*Width.*—6.0 cm to 9.0 cm.
*Lobes.*—Lobation characteristics: Moderately deep. Texture (both surfaces): Smooth. Vein color: Upper surface: Transparent. Lower surface: RHS 139D; middle vein is slightly reddish.
*Variegation.*—Absent.
*Venation pattern.*—Reticulate.
*Color.*—Mature foliage: Upper surface: RHS 139A. Lower surface: RHS 139D. Immature foliage: Upper surface: RHS 141A. Lower surface: RHS 139B.
*Leaf petiole.*—Length: 3.0 cm to 6.0 cm. Diameter: 0.2 cm to 0.3 cm. Color: Upper (part) surface: RHS 59A. Lower (part) surface: RHS 181B. Texture: Smooth. Strength: Medium.

Inflorescence:
*Lastingness of inflorescence on the plant.*—4 weeks.
*Natural flowering season.*—End of November.
*Diameter.*—27.0 cm to 30.0 cm.
*Height.*—3.0 cm to 4.0 cm.
*Fragrance.*—Absent.

Bracts:
*Number of bracts per inflorescence.*—6 to 9.
*Shape.*—Ovate.
*Apex.*—Acute.
*Base.*—Obtuse.
*Margin.*—Mostly entire but older bracts are slightly serrate.
*Size.*—Length: 9.0 cm to 11.0 cm. Width: 4.0 cm to 8.0 cm.
*Texture (both upper and lower surfaces).*—Smooth.
*Venation pattern.*—Reticulate.
*Vein color.*—Upper surface: RHS 59A. Lower surface: RHS 181B.
*Bract color.*—Upper surface: RHS 46B. Lower surface: RHS 47B.
*Bract petiole.*—Length: 0.5 cm to 2.5 cm. Diameter: 0.2 cm to 0.3 cm. Color: Upper (part) surface: RHS 59A. Lower (part) surface: RHS 181B. Texture: Smooth. Strength: Medium.

Cyme:
*Diameter.*—1.0 cm to 2.5 cm.
*Cyathia number.*—7 to 10 per inflorescence.
*Deformation of glands of the cyathium.*—Absent.
*Timing of opening of cyathia.*—Opens end of November; duration first pollen in parallel to opening of the nectar cups and stigmas appear 1 to 2 weeks later.
*Cyathium.*—Shape: Ovate. Diameter: 0.2 cm to 0.6 cm. Length: 0.3 cm to 0.8 cm. Color: RHS 143C.
*Peduncle.*—Color: RHS 142B. Length: 0.2 cm to 0.3 cm. Diameter: 0.1 cm. Texture: Smooth. Strength: Medium.
*Nectar cups.*—Number: 1 per cyathium. Diameter: 0.1 cm. Length: 0.4 cm to 0.5 cm. Color: RHS 1C.

Reproductive organs:
*Stamen quantity.*—5 to 10 per cyanthium.
*Stamen shape.*—Ovate.
*Filament length.*—0.25 cm.
*Filament color.*—RHS 46A.
*Pollen quantity.*—Moderate.
*Pollen color.*—RHS 12A.
*Gynoecium.*—Present. Pistil quantity per cyathium: 1. Pistil length: 0.2 cm. Stigma form: Divided in 2 parts. Stigma color: RHS 183A. Style length 0.2 cm. Style color: HS 183A. Ovary length: 0.05 cm. Ovary color: RHS 143C.

Fruit and seed set: None observed.

COMPARISON WITH PARENTAL LINE AND KNOWN VARIETY

'NPCW13218' is a distinct variety of Poinsettia having bright red bracts. 'NPCW13218' is distinguished from its parent 'NPCW 10164' as described in Table 1.

TABLE 1

| Characteristic | Variety 'NPCW13218' | Parent 'NPCW10164' |
|---|---|---|
| Bract color, upper surface | RHS 46B | RHS 46A |
| Bract color, lower surface | RHS 47B | RHS 47A |
| Leaf quantity per lateral branch | 6 to 7 | 8 to 15 |

'NPCW13218' can be compared to the commercial Poinsettia plant variety 'NPCW06115' (U.S. Plant Pat. No. 19,020). Differences between the two varieties are described in Table 2.

TABLE 2

| Comparison with Similar Variety | | |
|---|---|---|
| Characteristic | 'NPCW13218' | Commercial line 'NPCW06115' |
| Plant width or spread | 25.0 cm to 30.0 cm | 30.0 cm to 35.0 cm |
| Inflorescence diameter | 27.0 cm to 30.0 cm | 15.0 cm to 20.0 cm |

We claim:

1. A new and distinct variety of poinsettia plant named 'NPCW13218' as illustrated and described herein.

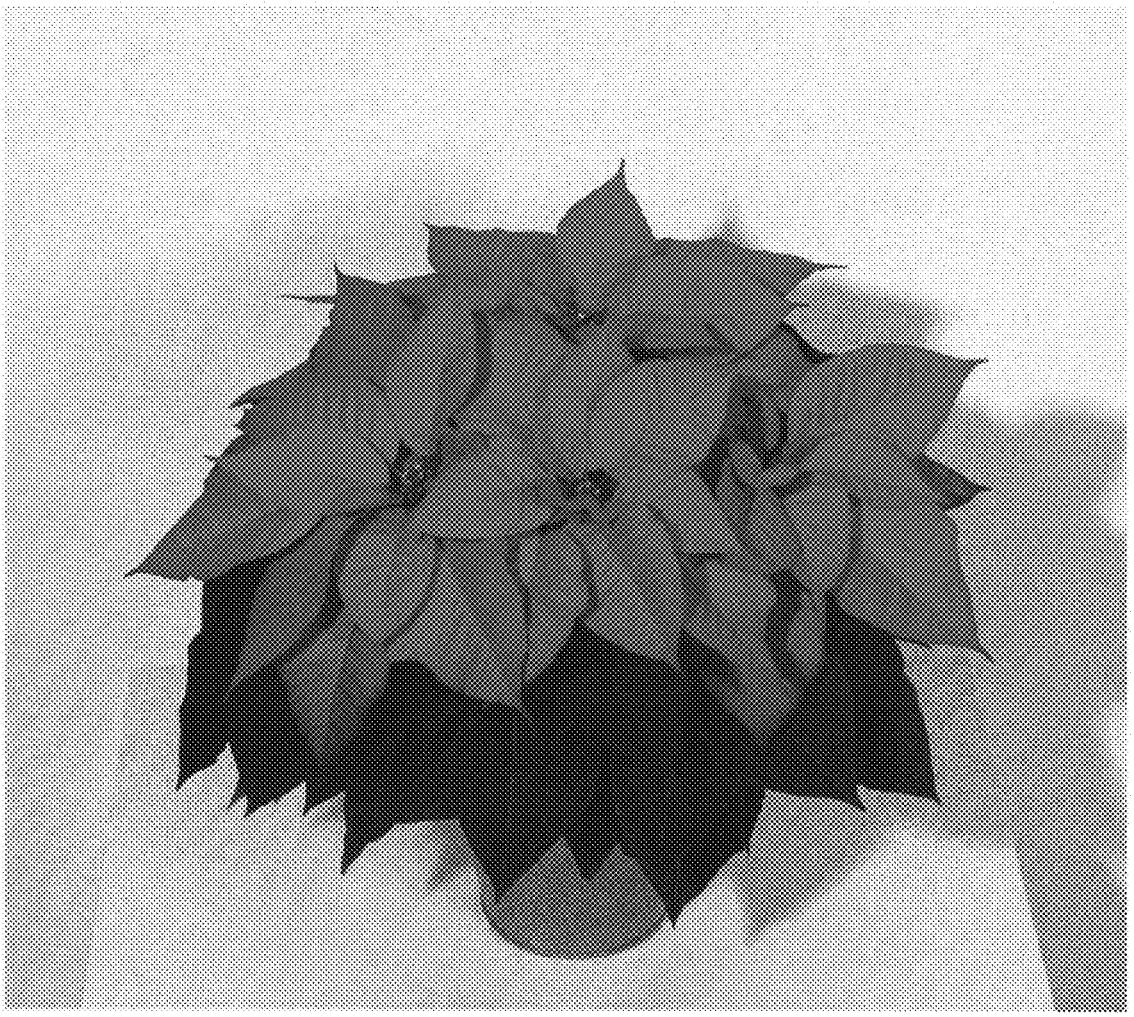

* * * * *